United States Patent
Segman

(10) Patent No.: US 10,687,739 B2
(45) Date of Patent: Jun. 23, 2020

(54) METHOD AND APPARATUS FOR NON-INVASIVE GLUCOSE MEASUREMENT

(71) Applicant: Cnoga Medical Ltd., Caesarea (IL)

(72) Inventor: Yosef Segman, Zichron Yaacov (IL)

(73) Assignee: Cnoga Medical Ltd., Caesarea (IL)

( * ) Notice: Subject to any disclaimer, the term of this patent is extended or adjusted under 35 U.S.C. 154(b) by 268 days.

(21) Appl. No.: 15/695,056

(22) Filed: Sep. 5, 2017

(65) Prior Publication Data
US 2019/0069821 A1 Mar. 7, 2019

(51) Int. Cl.
| | | |
|---|---|---|
| *A61B 5/145* | (2006.01) | |
| *A61B 5/1455* | (2006.01) | |
| *G01J 3/02* | (2006.01) | |
| *A61B 5/1495* | (2006.01) | |
| *A61B 5/00* | (2006.01) | |
| *G01N 21/359* | (2014.01) | |
| *G01N 29/02* | (2006.01) | |

(52) U.S. Cl.
CPC ........ *A61B 5/14532* (2013.01); *A61B 5/1455* (2013.01); *A61B 5/1495* (2013.01); *A61B 5/6826* (2013.01); *A61B 5/7264* (2013.01); *G01J 3/02* (2013.01); *G01N 21/359* (2013.01); *A61B 5/7275* (2013.01); *G01N 29/02* (2013.01)

(58) Field of Classification Search
CPC . A61B 5/14532; A61B 5/1455; A61B 5/6826; A61B 5/7275; A61B 5/1495; A61B 5/7264; G01J 3/02; G01N 29/02
See application file for complete search history.

(56) References Cited

U.S. PATENT DOCUMENTS

| | | | | |
|---|---|---|---|---|
| 5,910,109 | A | 6/1999 | Peters et al. | |
| 7,620,674 | B2 * | 11/2009 | Ruchti | A61B 5/14532 708/400 |
| 8,948,833 | B2 * | 2/2015 | Segman | A61B 5/14532 600/322 |
| 2010/0331637 | A1 | 12/2010 | Ting et al. | |

FOREIGN PATENT DOCUMENTS

| | | |
|---|---|---|
| CN | 106446777 | 2/2017 |
| WO | 02065090 | 8/2002 |
| WO | 2004069164 | 8/2004 |

\* cited by examiner

*Primary Examiner* — Christine H Matthews
*Assistant Examiner* — Joshua Daryl D Lannu
(74) *Attorney, Agent, or Firm* — Mark M. Friedman

(57) ABSTRACT

An apparatus for monitoring blood glucose comprising an invasive component for invasively measuring blood glucose and a non-invasive component, including color image sensor(s) to generate images from absorption of light that traversed the tissue, to receive a body part and generate a non-invasive blood glucose reading. Processor(s) convert the images into a vector V associated with a particular at least one invasive blood glucose measurement $g_{k1}$, form a regular learning matrix, $\lambda$, implement a noninvasive isolation mechanism of the tissue glucose level by unique association of the vector $V_k$ with an invasive blood glucose level, determine a neural network from the learning set $\lambda$ by pairing vectors into a branch and forming multiple branches into loops, wherein two vectors are paired if they have a pre-defined similarity in the blood glucose levels that each are associated with; and calibrate the neural network by having it pass at least one test.

21 Claims, 8 Drawing Sheets

FIG. 3 GLUCOSE MAP

METHOD AND APPARATUS FOR NON-INVASIVE GLUCOSE MEASUREMENT

FIELD AND BACKGROUND OF THE INVENTION

The present invention relates to apparatuses and methods for computing tissue glucose non-invasively Diabetes is a global health burden, declared by World Health Organization (WHO) as a global epidemic due to its rapidly growing prevalence. It is a chronic disease in which sugar levels are increased in the body due to either insufficient insulin production by the pancreas or un-effective usage of insulin by the body. The effects of diabetes include long-term damage, dysfunction and failure of various organs including the retina, kidney and vasculature.

Intensive management of blood glucose levels is crucial in diabetes management and treatment. The Diabetes Control and Complications Trial and the UK Prospective Diabetes Study follow-up showed that early, tight glucose control in people with Type 1 and Type 2 diabetes reduced the risk of development or progression of long-term diabetes complications.

Today, finger stick testing is the mainstay of blood glucose detection. Sufficient blood glucose monitoring requires frequent (more than four times a day) blood measurements accompanied by discomfort and pain.

The need for convenient blood glucose self-monitoring technique has led to the development of alternative technologies including the continuous and non-invasive monitoring. Continuous blood glucose devices require invasive sensor inserted under the skin, being replaced at least once or twice a month, which is inconvenient and expensive.

So far, several non-invasive methods including near-infrared spectroscopy, Raman spectroscopy, ultrasound and so forth were proposed, however no satisfactory solution was introduced to the market. Optical methods have failed to recognize blood glucose levels mainly because glucose has weak connection to light, e.g. visual to IR light. Moreover, it is highly unlikely to calibrate the entire worldwide population under universal calibration manifold with so many obstacles on the way, such as: tissue perfusion, tissue temperature, other blood substance, hemodynamic factors, skin color, nails, dry skin, etc. Furthermore, glucose is less than 0.1% of human tissue by weight. Therefore, variances due to thermal, mechanical, hemodynamics, optical, or other instabilities may interfere with the non-invasive glucose reading.

SUMMARY OF THE INVENTION

One aspect of the invention is a method of monitoring a blood glucose of a person, comprising (a) (i) invasively measuring the blood glucose of the person using an invasive component of a bioparameter monitoring device, storing an invasive blood glucose reading, $g_{k1}$, in a non-invasive component of the bioparameter monitoring device, and (ii) optionally repeating step "(a)(i)" to produce at least an additional invasive blood glucose measurement, $g_{k2}$, and if step "(a)(i)" is repeated, requiring $g_{k2}$ to be sufficiently close to $g_{k1}$ by a pre-defined measure of closeness; (b) within a proximity time before or after step "(a)", one or more color image sensors in the non-invasive component of the device generating a series of images reflecting absorption of light having traversed tissue of a body part of the person, the series of images converted into a vector V, wherein the vector V is associated with a particular at least one invasive blood glucose measurement $g_{k1}$, representing a momentary glucose level in the person's blood and the set of all vectors V associated with an invasively determined blood glucose level define the learning set λ of the device; from a plurality of learning vectors, forming, by the one or more processors, an M by N regular learning matrix, λ, by repeating steps "(a)" through "(b)" so as to acquire N vectors in the learning set, wherein N is determined according to the person's invasively determined blood glucose level; (c) implementing a noninvasive isolation mechanism of the tissue glucose level by unique association of the vector $V_k$ with an invasive blood glucose level, wherein the association is defined as $V_k \rightarrow g_k$, wherein if $V_k = V_n$ then $g_k = g_n$ for any k≠n, where $g_k$ and $g_n$ are the invasively determined blood glucose level references of the person and $V_k$ is a vector in the learning set λ, and discarding vectors $V_k$ that fail the noninvasive isolation association; (d) determining, by the one or more processors, a neural network from the learning set λ by pairing vectors into a branch and forming multiple branches into loops, wherein two vectors are paired if they have a pre-defined similarity in the blood glucose levels that each are associated with; and (e) calibrating the neural network by having the neural network pass at least one internal blind test.

Another aspect of the invention is an apparatus for monitoring a blood glucose of a person, comprising (a) an invasive component configured for (i) invasively measuring the blood glucose of the person using an invasive component of a bioparameter monitoring device, storing an invasive blood glucose reading, $g_{k1}$, in a non-invasive component of the bioparameter monitoring device, and for (ii) optionally repeating the invasive measurement of "(i)" to produce at least an additional invasive blood glucose measurement, $g_{k2}$, and if step "(a)(i)" is repeated, requiring $g_{k2}$ to be sufficiently close to $g_{k1}$ by a pre-defined measure of closeness; (b) a non-invasive component structured to receive a body part of the person and configured to generate a non-invasive blood glucose reading of tissue of the body part-upon insertion of the body part of the patient into the non-invasive component, the non-invasive component including one or more color image sensors configured to generate a series of images reflecting absorption of light that traversed the tissue, the device having one or more processors programmed using program code to: convert the series of images into a vector V, wherein the vector V is associated with a particular at least one invasive blood glucose measurement $g_{k1}$, representing a momentary glucose level in the person's blood and the set of all vectors V associated with an invasively determined blood glucose level define the learning set λ of the device; form, from a plurality of learning vectors, an M by N regular learning matrix, λ, by using an output of repeated invasive measurements both of "(a)" and the non-invasive biometric reading of the tissue of "(b)" so as to acquire N vectors in the learning set, wherein N is determined according to the person's invasively determined blood glucose level; implement a noninvasive isolation mechanism of the tissue glucose level by unique association of the vector $V_k$ with an invasive blood glucose level, wherein the association is defined as $V_k \rightarrow g_k$, wherein if $V_k = V_n$ then $g_k = g_n$ for any k≠n, where $g_k$ and $g_n$ are the invasively determined blood glucose level references of the person and $V_k$ is a vector in the learning set λ, and discard vectors $V_k$ that fail the noninvasive isolation association; determine a neural network from the learning set λ by pairing vectors into a branch and forming multiple branches into loops, wherein two vectors are paired if they have a pre-defined similarity in the blood glucose levels that each are associated with; and calibrate the neural network by having the neural network pass at least one internal blind test.

A still further aspect of the invention is a non-transitory computer-readable medium having stored thereon glucose monitoring software, the glucose monitoring software executed by one or more processors, the execution of the glucose monitoring software by the one or more processors performing: storing an invasive blood glucose reading, $g_k$, in a non-invasive component of a glucose monitoring device, and optionally storing an additional invasive blood glucose reading, $g_{k2}$, and if optional storing occurs, requiring $g_{k2}$ to be sufficiently close to $g_{k1}$ by a pre-defined measure of closeness; receiving a series of images from one or more color image sensors reflecting absorption of light that traversed tissue of a body part of a person, converting the series of images into a vector V, wherein the vector V is associated with a particular at least one invasive blood glucose measurement $g_{k1}$, representing a momentary glucose level in the person's blood and the set of all vectors V associated with an invasively determined blood glucose level define the learning set λ of the device; forming, from a plurality of learning vectors, an M by N regular learning matrix, λ, by using an output of repeated invasive measurements both of "(a)" and the non-invasive biometric reading of the tissue of "(b)" so as to acquire N vectors in the learning set, wherein N is determined according to the person's invasively determined blood glucose level; implementing a noninvasive isolation mechanism of the tissue glucose level by unique association of the vector $V_k$ with an invasive blood glucose level, wherein the association is defined as $V_k \rightarrow g_k$, wherein if $V_k = V_n$ then $g_k = g_n$ for any k≠n, where $g_k$ and $g_n$ are the invasively determined blood glucose level references of the person and $V_k$ is a vector in the learning set λ, and discard vectors $V_k$ that fail the noninvasive isolation association; determining a neural network from the learning set λ by pairing vectors into a branch and forming multiple branches into loops, wherein two vectors are paired if they have a pre-defined similarity in the blood glucose levels that each are associated with; and calibrating the neural network by having the neural network pass at least one internal blind test.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a medical apparatus and method configured, once calibrated, to generate non-invasive blood glucose readings. The device enables measuring noninvasively tissue glucose concentration and invasively capillary blood glucose concentration. Noninvasive glucose readings usually provide irregular or disordered mathematical manifold over the measurement space, therefore it is most unlikely to establish a transfer function that relates between the noninvasive raw data and the actual true invasive glucose level. In order to overcome this major problem the device has features, as described below, including a program code that interfaces with the two components of the device to utilize an associative mathematical concept. Furthermore, instead of universal or cluster calibration, a personal calibration technique is used. The device facilitates diabetes management and enables more efficient and painless patient care.

Figures 1A, 1B:
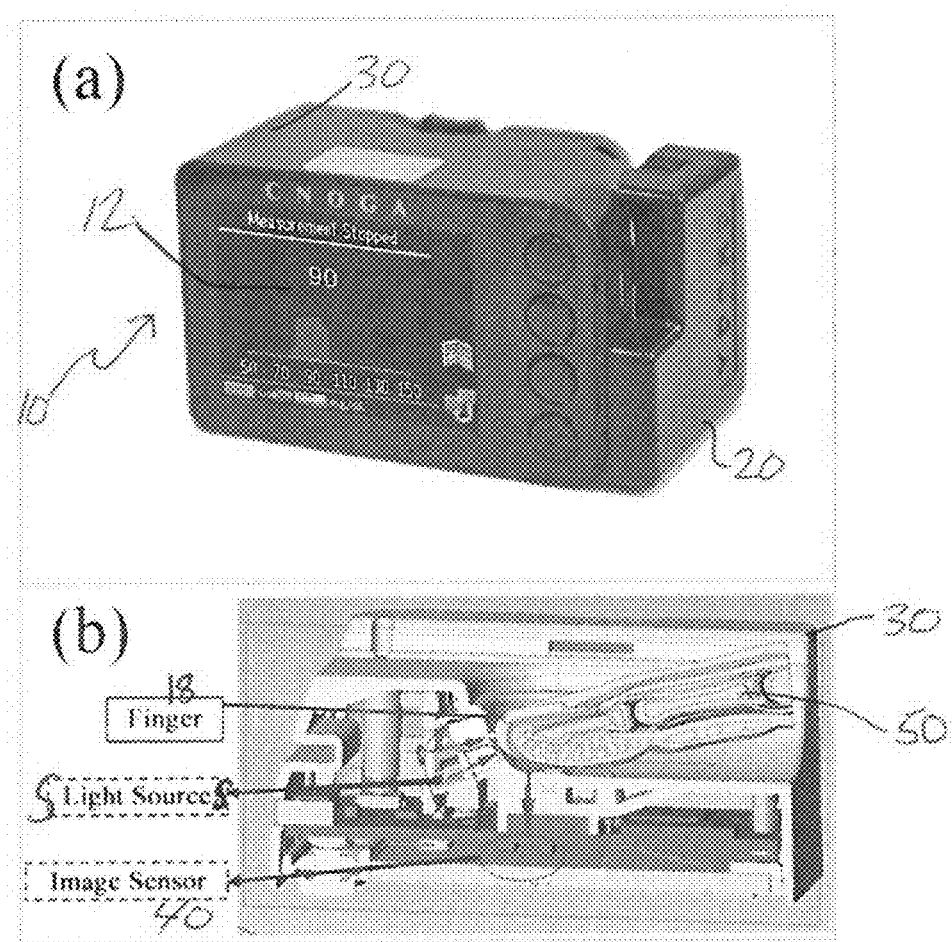
FIG. 1A is a photograph of a device, in accordance with one embodiment of the invention.
FIG. 1B is a cross-sectional view of the device of FIG. 1, in accordance with one embodiment of the invention.

The device of the invention is small, light-weight and portable device, as can be seen in FIG. 1A. The device is intended for use in the home environment and as well as an additional support in clinics. In certain embodiments, the device comprises medical and control subsystems. The medical subsystem contains a color image sensor, LEDs and a DSP which is responsible for the image acquisition, the image processing, the lighting control system and the extraction of the clinical parameters values. The control subsystem contains four touch-buttons, a display, an audio-speaker and a Microcontroller Unit (MCU) which is in charge of the user interface, the process management, the internal storage and the device's power management. As described in FIG. 1B, the device 10 may have a finger compartment, four monochromatic light sources in the visual to IR spectrum (~600 nm to ~1000 nm), one or more color image sensors and an invasive glucometer add-on module (invasive component 20). The add-on module is used for calibrating the noninvasive component. In some cases, the medical and control subsystems are embedded in a single processor such as DSP or microcontroller.

The technology is based on a color image sensor. The device in some embodiments uses a real time color image sensor which provides the ability to analyze tissue pigmentation over spatial-temporal-color domain. Color image sensors provides richer information compared to other known devices, such as a standard pulse oximetry. The pulse oximeter usually uses two discrete diode sensors and two monochromatic light sources. The device uses 4 monochrome light source and color image sensor absorbing continuous wavelength light usually in the range from blue to IR. The color image raw data is acquired by the color image sensor and stored in a memory buffer to be used for the computation of a dedicated algorithm executed in the device DSP component.

As shown in FIG. 1, the device 10 comprises a one or more color image sensors 40 in some embodiments rather than discrete sensors. The one or more color image sensors 40 in some embodiments represents continuous absorption that vary from 350 nm up to 1000 nm in three color planes, i.e. red, green and blue. Such sensor provides insight into the color-special-temporal space. In one embodiment, a simple color image sensor was used. In some other embodiments, device 10 includes an additional matrix sensor. The device 10, in certain embodiments, utilizes personal calibration instead of universal calibration. Nonetheless, once sufficient post marketing knowledge has been gathered, a cluster or universal calibration may be considered. The device also employs the principle in some embodiments that a single vector representing temporary absorption shall not represent two relatively different glucose levels.

The principles and operation of a Method and Apparatus for Non-Invasive Glucose Measurement may be better understood with reference to the drawings and the accompanying description.

Figure 4:
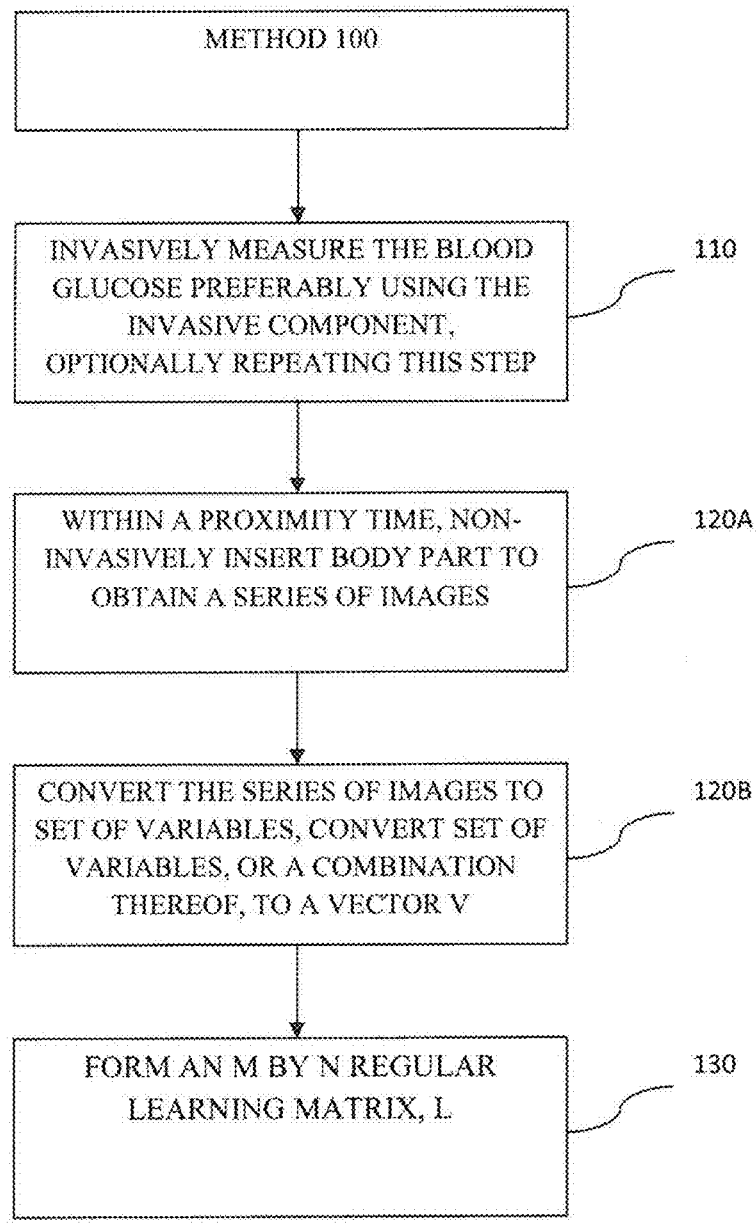
FIG. 4 is a flowchart showing a method in accordance with one embodiment of the invention.
Figure 4:
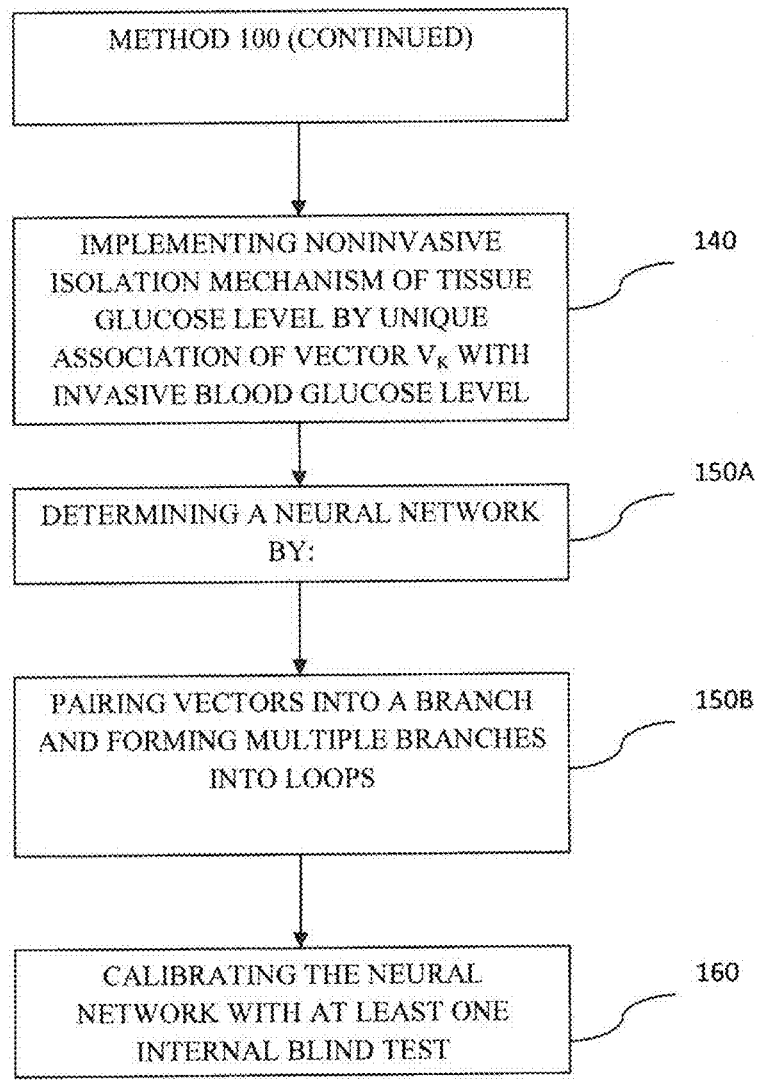

As shown in FIG. 4, a method 100 of monitoring a blood glucose of a person, according to one embodiment, comprises a step 110 of (i) invasively measuring the blood glucose of the person using an invasive component of a bioparameter monitoring device 10, storing an invasive blood glucose reading, $g_{k1}$, in a non-invasive component of the bioparameter monitoring device, and (ii) optionally repeating step "(i)" to produce at least an additional invasive blood glucose measurement, $g_{k2}$, and if step "(i)" is repeated, requiring $g_k$ to be sufficiently close to $g_{k1}$ by a pre-defined measure of closeness.

As a further step 120A of method 100, within a proximity time, for example between one and 7 minutes, before or after step 110, one or more color image sensors 15 in the non-invasive component of the device 10 generates a series of images reflecting absorption of light having traversed the tissue. In step 120B, the series of images may be converted into a vector V (for example by converting the series of images into a set of variables, and converting the set of variables, or a combination thereof, into a vector V or in other examples by converting directly into a vector V), wherein the vector V is associated with a particular at least one invasive blood glucose measurement $g_{k1}$, representing a momentary glucose level in the person's blood. The set of all vectors V associated with an invasively determined blood glucose level define the learning set λ of the device (note that the notation "λ" for "learning set" is not related to the notation "L" for monochrome light as used below).

Constructing a vector, $V_k$ is performed according to one particular embodiment as follows, as shown in this example:

1. Let $r_n(x,y,t)$, $g_n(x,y,t)$ and $b_n(x,y,t)$ be the three spatial-temporal-color video stream representing the absorption levels of the capillary tissue under consideration illuminated by a set of monochrome light ($L_{in}$) having emission levels ($e_{in}$) where i=1, 2, 3, 4 represents a wavelength index and n represents set of light combination 1≤n≤N.
   Example:
   n=1; i=1, 2, 3, 4
   $L_{11}$=625 nm LED emitted at $e_{11}$ milliamp
   $L_{21}$=740 nm LED emitted at $e_{21}$ milliamp
   $L_{31}$=850 nm LED emitted at $e_{31}$ milliamp
   $L_{41}$=940 nm LED emitted at $e_{41}$ milliamp n=2; i=1, 2, 3, 4
   $L_{12}$=625 nm LED emitted at $e_{12}$ milliamp
   $L_{22}$=740 nm LED emitted at $e_{22}$ milliamp
   $L_{32}$=850 nm LED emitted at $e_{32}$ milliamp
   $L_{42}$=940 nm LED emitted at $e_{42}$ milliamp
   Each set of light n corresponds to a set of real time images $r_n(x,y,t)$, $g_n(x,y,t)$ and $b_n(x,y,t)$ wherein for n=1 it corresponds to $r_1(x,y,t)$, $g_1(x,y,t)$ and $b_1(x,y,t)$ and for n=2 it corresponds to $r_2(x,y,t)$, $g_2(x,y,t)$ and $b_2(x,y,t)$.

2. Let $U_{kn}$ be a feature-vector associated with invasive whole blood glucose level $g_k$ and set of lights n=1 ... N. k denotes the index of the $k^{th}$ feature vector in the device log file.

3. Let $V_k$ be a feature-vector composed by $\{U_{kn}\}$, i.e. $V_k = \{(U_{k1}, U_{k2}, U_{k3}, \ldots, U_{kn})\}$. Taking under consideration the upper example, the vector $V_1$ i.e. k=1 is composed by two sub vectors $U_{11}$ and $U_{12}$ i.e. $V_1 = (U_{11}, U_{12})$ where the subsector $U_{11}$ represents the absorption response to $L_{i1}$ set of light emission and $U_{12}$ to $L_{i2}$ set of light emission.

The process of pre-scheduled noninvasive data collection is represented by a set of vectors versus true invasive readings. A suggested personal calibration is achieved by designing optimal personal pre schedule glucose readings. Blood pigment may vary between people. In addition, for a given person, blood pigment may vary depending on the time of day, for example waking time, morning, noon time, evening, night time. In another example, blood pigment may change from before a meal to after the meal. Therefore, in one particular non-limiting embodiment, one makes reference tests eight times a day for seven days resulting in fifty-six pre-scheduled calibrations made of reliable references. In certain embodiments, during the calibration period two standard-conventional strips for 'double-check' per each non-invasive sample vector V are used as reference. This schedule is based on the fact that blood pigmentation is varying during the day (wakening time, morning, noon time, evening, night time and before and after meals). This process of establishing the personal pattern (personal calibration process) may take around fifty-six reference tests (each reference test is using two strip readings) in order to achieve the most accurate pattern, in this particular embodiment. If the two strip readings are not sufficiently close to each other, the non-invasive sample vector is declared internally by the system as 'bad reference'. The advantage of personal calibration versus universal calibration is that the personal pattern takes into consideration the individual user's 'interfering factors'.

As shown in FIG. 4, method 100 may also comprise a step 130 in which an M by N regular learning matrix is formed by the one or more processors. The matrix is formed from a plurality of learning vectors by repeating steps "110" and "120" so as to acquire N vectors in the learning set. The number N is determined according to the person's invasively determined blood glucose level. For example, if the person has a severe case of diabetes and the person's glucose is normally high, such as in the 200's, the number of vectors N in the learning set λ will be greater. If, on the other hand, the subject's glucose level tends to be lower because he has a mild version of diabetes, N would be lower since fewer vectors are needed in the learning set λ.

Method 100 may also comprise a step 140 of implementing a noninvasive isolation mechanism of the tissue glucose level by unique association of the vector $V_k$ with an invasive blood glucose level, wherein the association is defined as $V_k \rightarrow g_k$, wherein if $V_k = V_n$ then $g_k = g_n$ for any k≠n, where $g_k$ and $g_n$ are the invasively determined blood glucose level references of the person and $V_k$ is a vector in the learning set L. In addition, vectors $V_k$ that fail the noninvasive isolation association are discarded.

The most difficult part in constructing non-invasive bio marker reading is the isolation of the bio marker. The non-invasive glucose isolation is achieved by associating a vector V to a single glucose level. The vector components are based on the information gathered by the color image sensor. Accordingly, two non-identical vectors representing temporary light absorption traverse the tissue under consideration may represent identical or almost identical glucose level, however, two identical or almost identical vectors will represent single glucose level.

Figure 3:
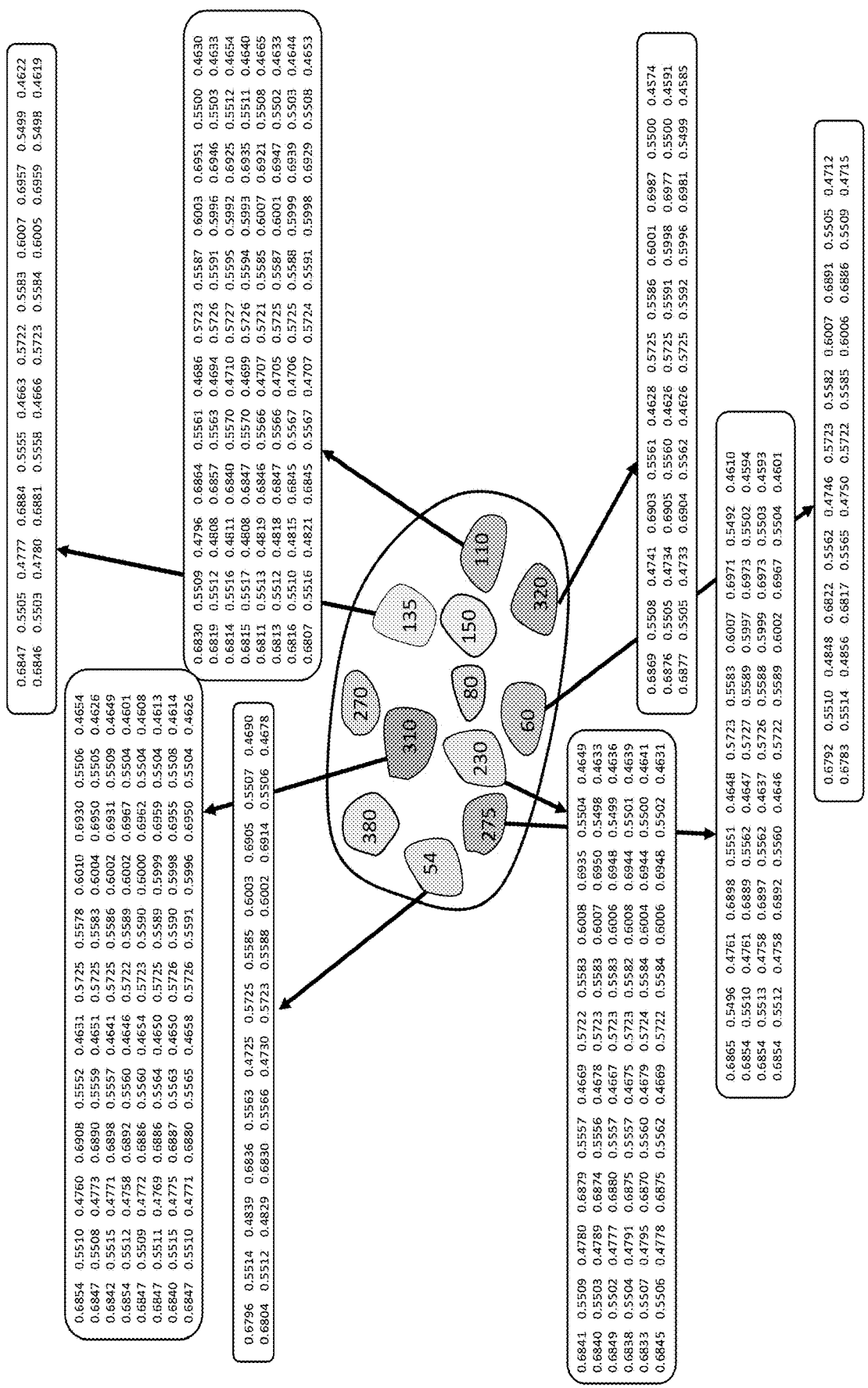
FIG. 3 is a personal glucose map associated with the non-invasive sample vectors, wherein the vectors represent partial information, in accordance with one embodiment of the invention.

One of the approaches for achieving order from disorder is by using an association mechanism in a similar way to the brain neural mechanism. The current adaptive learning machine associates groups of vectors to various glucose levels. The association is not unique, a single glucose level may associate to one or more vectors. However, each vector has a unique association to glucose level (the isolation mechanism), i.e. a single vector cannot be associated with two different glucose levels. FIG. 3 describes various synchronized groups of vectors associated with various glucose values.

Regarding steps 110 and 140 of method 100, in some embodiments, each non-invasive reading produces a sample vector $V_k$, associated with two invasive blood glucose measurements (rather than one invasive blood glucose measurement where the measurement is repeated optionally) using standard-conventional strips sufficiently close to each other, namely $g_{k1}$ and $g_{k2}$. This association is considered the "Isolation Mechanism" of the tissue glucose. For example, $$V_k \longleftrightarrow (g_{k1}, g_{k2}) \quad (1)$$

A fundamental requirement of (1) (i.e the isolation mechanism) is the independence of the vector set $\{V_k\}$. Independence means that there are no two vectors sufficiently close to each other i.e. $V_k = V_n$ for $k \neq n$ resulting with two different (i.e. not sufficient close) glucose levels. In mathematical terms:

$$\text{If } V_k = V_n \text{ then } g_k = g_n \text{ for any } k \neq n \quad (2)$$

where $g_k$ and $g_n$ are the actual glucose level references acquired by the invasive component of the device.

Method 100 may include a further step 150 of determining, by the one or more processors, a neural network from the learning set λ by pairing vectors into a branch and forming multiple branches into loops, wherein two vectors are paired if they have a pre-defined similarity in the blood glucose levels that each are associated with (for example the glucose levels of each of the two vectors are sufficiently close to one another).

In one example, adaptive machine learning includes the following association rules. Non-invasive signals are chaotically related to glucose over the Euclidean $R^n$ space. Therefore an association approach which imitates a neural network is suggested. The following provides the general rules of the neural network, in accordance with one embodiment of the invention.

1. Valid Sample Vector:
A vector $V_k$ associated with two invasive references is a valid sample vector if the two references are sufficient close to each other and the vector itself passes all the internal requirements in order to internally declare its validity.

2. New Vector Insertion into the Learning Set:
A new vector $V_{new}$ is being inserted into the learning set if $V_{new}$ is independent from all previous vectors in the calibration set L.

3. Removing a Vector from the Learning Set L:
A Vector $V_k$ shall be removed from the neural network if it becomes useless (obsolete).

4. Tree, Branches, Loops, Groups and Association:
The current neural network may have connections in all directions (forward, backward, left or right) generating branches and loops. Relationship between various vectors generating open and/or close loops.

Figure 2:
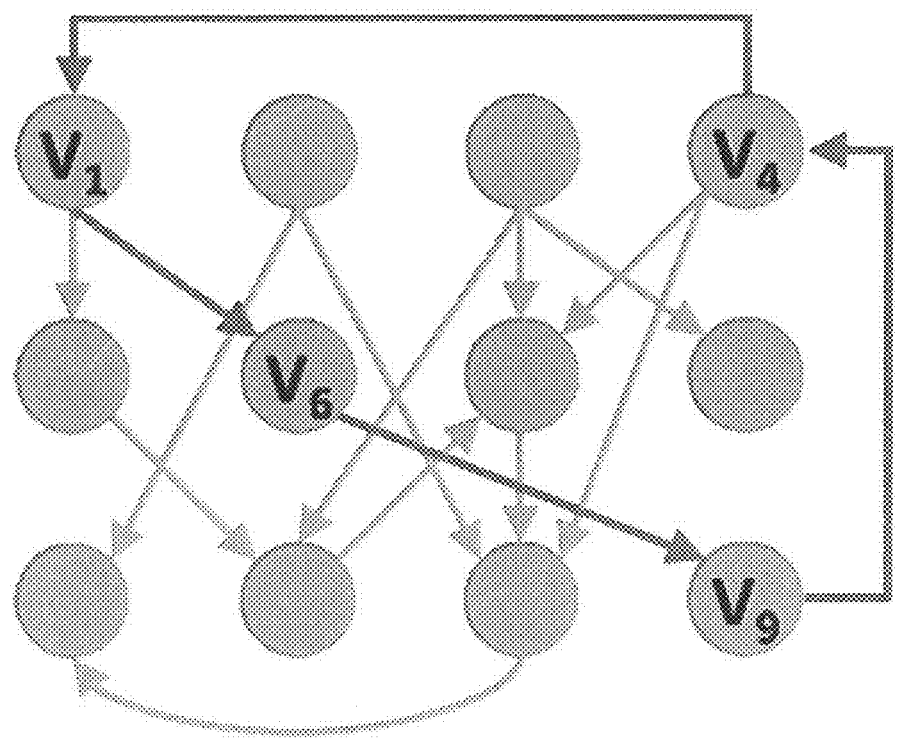
FIG. 2 is a schematic illustration of a non-limiting example of a closed loop vector association used in a non-invasive component of a device, in accordance with one embodiment of the invention.

A branch is the association or connection between two vectors. A closed loop is giving by the connections $V_1 \rightarrow V_6 \rightarrow V_9 \rightarrow V_4 \rightarrow V_1$ as depicted in FIG. 2. An open loop is a set of connected vectors (branches) that does not end in a closed loop. A tree is a set of branches having a single origin. In some embodiments, a weighting function (or a weight) is associated with a branch depending on a glucose or other bio marker level, time of measurement, tissue temperature, etc. A "group" is a set of connected vectors with an open or closed loop fulfilling certain conditions.

Method 100 may include a further step 160 of calibration tests of the neural network by having the neural network pass at least one internal blind test.

In accordance with certain embodiments, a learning set λ includes N pre-scheduled measurements, whereas N, depends on the severity of patient's illness. In this embodiment the calibration process is based on two tests:
1. Calibration incorporating about 70% of the entire valid sample vectors in the learning log file is used to generate a neural network. The 30% of the remaining sample vectors are being used for the internal blind test and are considered as a set of new vectors $\{V^{new}\}$. This subset is tested and correlated to the optimal loop of vectors in the basic learning set. If the blind test on the remaining 30% passes the required accuracy, a second test is performed on the entire learning set (70%+30%) as described immediately below.
2. A subset $\{A_k = (V_1, \ldots V_{k-1}, V_{k+1}, \ldots, V_n)\}$ of valid sample vectors excluding the vector $V_k$ is temporarily used to generate a neural network. The excluded vector $V_k$ is now being used for internal blind test and is considered as a new vector $V^{new}$. The vector is tested and correlated to the optimal loop of vectors in subset $A_k$. In certain embodiments, this process is repeated among all other valid sample vectors.

Figure 6:
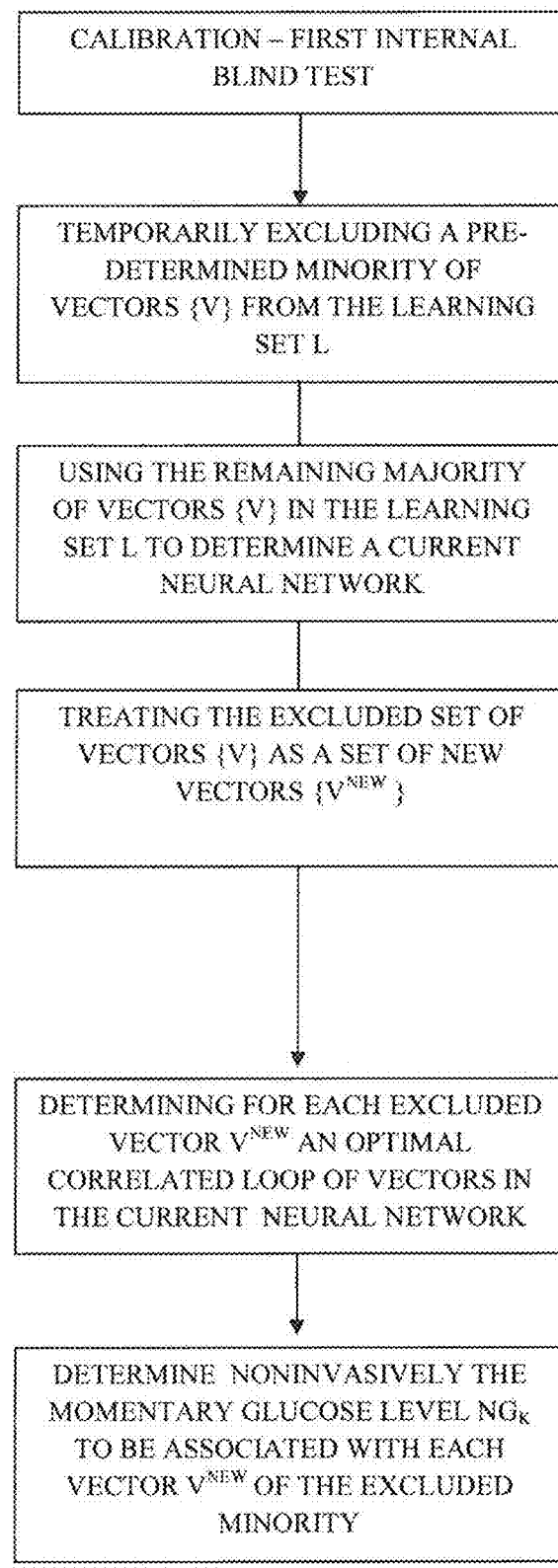
FIG. 6 is a flow chart showing steps of a first internal blind test for calibration, in accordance with one embodiment of the invention.

Accordingly, in some embodiments of step 160, the first internal blind test, as shown in FIG. 6, comprises (a) temporarily excluding a pre-determined minority of vectors $\{V\}$ from the learning set λ and the remaining majority of vectors $\{V\}$ in the learning set λ is used to determine a current neural network while treating the excluded set of vectors $\{V\}$ as a set of new vectors $\{V^{new}\}$ and (b) determining for each excluded vector $V^{new}$ an optimal correlated loop of vectors in the current neural network wherein the invasive glucose levels previously associated with the optimal correlated loop is used to determine noninvasively the momentary glucose level $ng_k$ to be associated with each vector $V^{new}$ of the excluded minority as the noninvasive reading.

Figure 7:
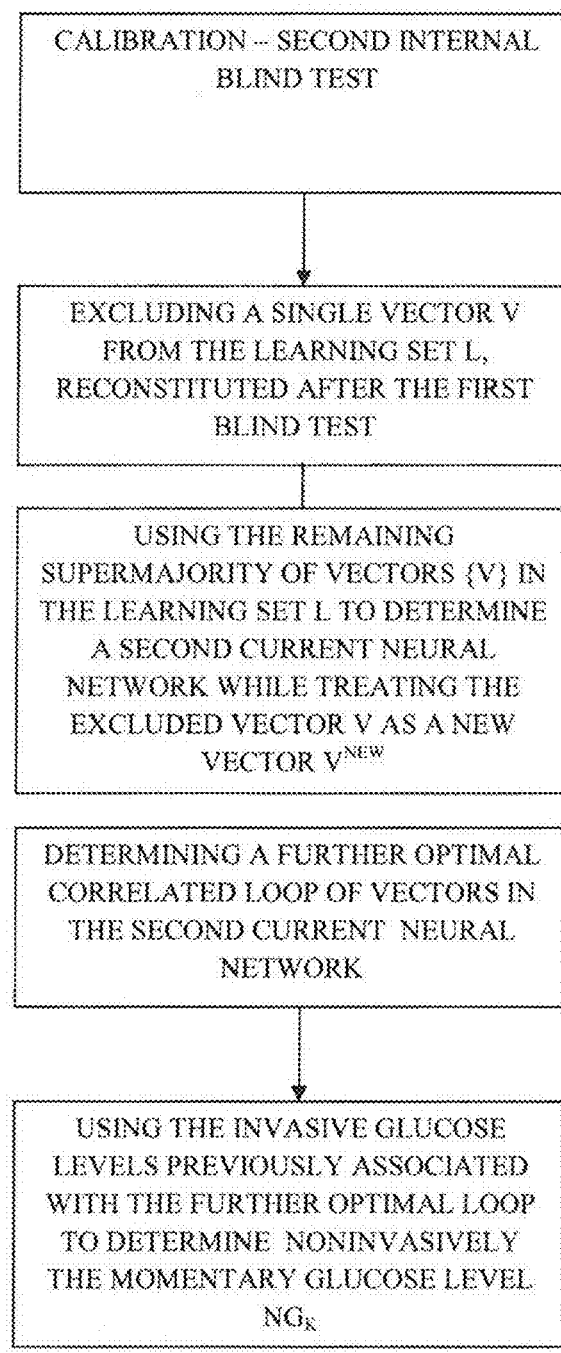
FIG. 7 is a flow chart showing steps of a second internal blind test for calibration, in accordance with one embodiment of the invention.

Method 100 may comprise performing a second internal blind test, as shown in FIG. 7, by:
(a) excluding a single vector V from the learning set λ, reconstituted after the first blind test, wherein the remaining supermajority of vectors $\{V\}$ in the learning set λ is used to determine a second current neural network while treating the excluded vector V as a new vector $V^{new}$ and (b) determining a further optimal correlated loop of vectors in the second current neural network and using the invasive glucose levels previously associated with the further optimal loop to determine noninvasively the momentary glucose level $ng_k$.

In some embodiments, the second internal blind test is repeated cyclically for all vectors in the learning set λ.

Calibration completed and post calibration: If the learning set λ satisfies the "calibration complete" requirements then the device is ready to perform non-invasive reading independently from the invasive component. Accordingly, in some embodiments of method 100, the device 10 is declared calibrated if the first and second internal blind tests pass an internal accuracy requirement defined by the differences between the noninvasive reading $ng_k$ and the invasive reading $g_k$ associated with each vector in the learning set L.

Method 100 may include a step of post-calibrating the device by, the one more processors obtaining, a new vector, $V^{new}$ by non-invasively measuring a body location of the person by using the one or more color image sensors in the non-invasive component to generate a series of images acquired from the one or more color image sensors of tissue of the body part, and converting the series of images into a new vector $V^{new}$, and finding an optimal correlated loop of the calibrated neural network with the new vector, $V^{new}$ and using the invasive glucose levels $g_k$ associated with the vectors in the optimal correlated loop of the calibrated neural network to compute noninvasively the glucose level $ng_{new}$ to be associated with the new vector $V^{new}$.

FIG. 3 is a personal Glucose Map associated with the non-invasive sample vectors. The vectors represent partial information. FIG. 3 describes the mechanism determining the personal glucose map associated with an individual. The circles in the center describing the invasive blood glucose measurements and the peripheral squares describe the associated vector branches $\{V_k\}$.

Post calibration represents an adaptive learning machine that from time to time adds new reference data based on the spatial-temporal statutory situation of the learning set. For example, in accordance with one embodiment, customers would calibrate the device by one non-invasive measurement followed by two invasive measurements taken by the invasive component (add-on detachable module 12) of the device 10. The customers would continue measuring themselves.

Figure 5:
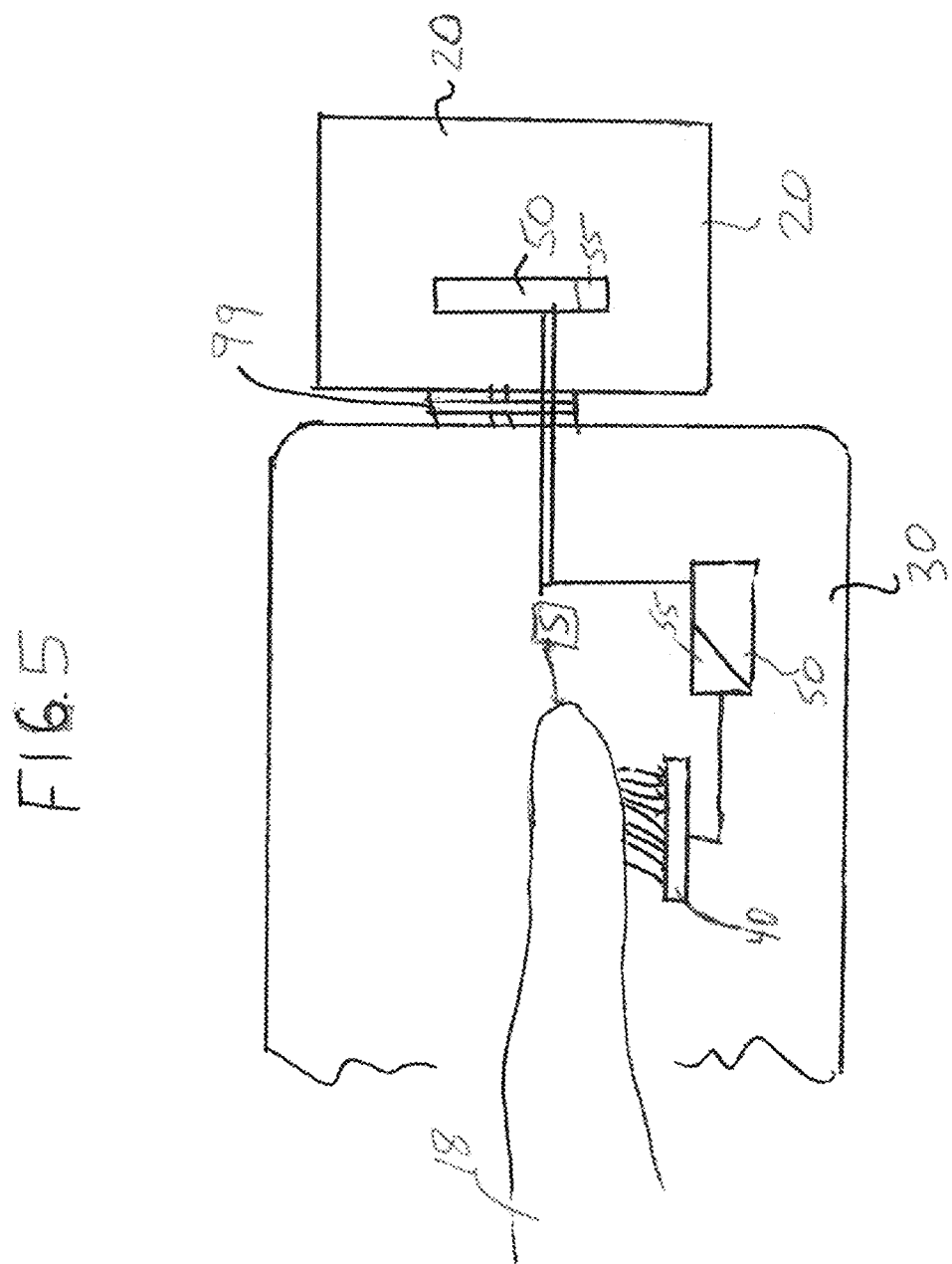
FIG. 5 is a schematic illustration of the internal processing of the device, in accordance with one embodiment of the invention.

As shown in the schematic illustration of FIG. 5, one embodiment of the invention is an apparatus 10 for monitoring a blood glucose of a person. Apparatus 10 may comprise, in one embodiment, (a) an invasive component 20 that may be configured for (i) invasively measuring the blood glucose of the person and storing an invasive blood glucose reading, $g_{k1}$, in a non-invasive component 20, and for (ii) optionally repeating the invasive measurement of "(i)" to produce at least an additional invasive blood glucose measurement, $g_{k2}$. FIG. 5 shows light from a light source traversing a body part 18 of a person, the light then impacting at least one color image sensor 40 that is connected to one or more processors 50 of a non-invasive component 30 of device 10.

As shown in FIG. 5, apparatus 10 also comprises a non-invasive component 30 structured to receive a body part 18 of a patient and configured to generate a non-invasive bioparametric reading of tissue of the body part upon insertion of the body part of the patient into the non-invasive component 30, the non-invasive component including one or more color image sensors 40 configured to generate a series of images reflecting absorption of light (from a light source S) having traversed the tissue of the body part of the person, to convert the series of images into a vector V (for example by converting the series of images to a set of variables and converting the set of variables, or a combination thereof, in a vector V, or in other examples, by converting the series of images directly into a vector V). Certain embodiments of the invention (FIG. 5) include a coupling component 99 between the invasive component 20 and the non-invasive component 30.

Device 10 may have one or more processors 50 programmed using program code 55 to:

(I) require $g_{k2}$ to be sufficiently close to $g_{k1}$ by a pre-defined measure of closeness if such an additional invasive blood glucose measurement, $g_{k2}$, is received and stored, (II) convert the series of images into a vector V (for example by converting the series of images into a set of variables and converting the set of variables, or a combination thereof, into a vector V or in other examples by converting the series of images directly into a vector V), wherein the vector V is associated with a particular at least one invasive blood glucose measurement $g_{k1}$, representing a momentary glucose level in the person's blood and the set of all vectors V associated with an invasively determined blood glucose level define the learning set λ of the device;

(III) form, from a plurality of learning vectors, an M by N regular learning matrix, λ, by using an output of repeated invasive measurements both of "(a)" and the non-invasive biometric reading of the tissue of "(b)" so as to acquire N vectors in the learning set, wherein N is determined according to the person's invasively determined blood glucose level;

(IV) implement a noninvasive isolation mechanism of the tissue glucose level by unique association of the vector $V_k$ with an invasive blood glucose level, wherein the association is defined as $V_k \rightarrow g_k$, wherein if $V_k = V_n$ then $g_k = g_n$ for any k≠n, where $g_k$ and $g_n$ are the invasively determined blood glucose level references of the person and $V_k$ is a vector in the learning set λ, and discard vectors $V_k$ that fail the noninvasive isolation association;

(V) determine a neural network from the learning set λ by pairing vectors into a branch and forming multiple branches into loops, wherein two vectors are paired if they have a pre-defined similarity in the blood glucose levels that each are associated with (for example the glucose levels of each of the two vectors are sufficiently close to one another); and (VI) calibrate the neural network by having the neural network pass at least one internal blind test.

In some embodiments of the apparatus 10, the one or more processors 50 are also programmed using program code 55 to conduct a first internal blind test, of the at least one internal blind test, comprising: (a) temporarily excluding a pre-determined minority of vectors {V} from the learning set λ and the remaining majority of vectors {V} in the learning set λ is used to determine a current neural network while treating the excluded set of vectors {V} as a set of new vectors $\{V^{new}\}$ and (b) determining for each excluded vector $V^{new}$ an optimal correlated loop of vectors in the current neural network wherein the invasive glucose levels previously associated with the optimal correlated loop is used to determine noninvasively the momentary glucose level $ng_k$ to be associated with each vector $V^{new}$ of the excluded minority as the noninvasive reading.

In some embodiments, the one or more processors are also programmed using program code to conduct a second internal blind test by (a) excluding a single vector V from the learning set λ, reconstituted after the first blind test, wherein the remaining supermajority of vectors {V} in the learning set λ is used to determine a second current neural network while treating the excluded vector V as a new vector $V^{new}$ and (b) determining a further optimal correlated loop of vectors in the second current neural network and using the invasive glucose levels previously associated with the further optimal loop to determine noninvasively the momentary glucose level $ng_k$.

In some embodiments, the second internal blind test is repeated cyclically for all vectors in the learning set λ. In some embodiments, the device is declared calibrated if the first and second internal blind tests pass an internal accuracy requirement defined by the differences between the noninvasive reading $ng_k$ and the invasive reading $g_k$ associated with each vector in the learning set λ.

In some embodiments, the one or more processors are also programmed using program code to post-calibrate the device by obtaining, a new vector, $V^{new}$ by non-invasively measuring a body location of the person by using the one or more color image sensors in the non-invasive component to generate a series of images acquired from the one or more color image sensors of tissue of the body part, and converting the series of images into a new vector $V^{new}$, and finding an optimal correlated loop of the calibrated neural network with the new vector, $V^{new}$ and using the invasive glucose levels $g_k$ associated with the vectors in the optimal correlated loop of the calibrated neural network to compute noninvasively the glucose level $ng_{new}$ to be associated with the new vector $V^{new}$.

Another embodiment of the invention is a non-transitory computer-readable medium having stored thereon glucose monitoring software, the glucose monitoring software executed by one or more processors, the execution of the glucose monitoring software by the one or more processors performing:

storing an invasive blood glucose reading, $g_{k1}$, in a non-invasive component of a glucose monitoring device, and optionally storing an additional invasive blood glucose reading, $g_{k2}$, and if optional storing occurs, requiring $g_{k2}$ to be sufficiently close to $g_{k1}$ by a pre-defined measure of closeness;

receiving a series of images from one or more color image sensors reflecting absorption of light that traversed tissue of a body part of a person, converting the series of images into a vector V (for example by converting the series of images into a set of variables, and converting the set of variables, or a combination thereof, into a vector V, or in other examples by converting directly into a vector V), wherein the vector V is associated with a particular at least one invasive blood glucose measurement $g_{k1}$, representing a momentary glucose level in the person's blood and the set of all vectors V associated with an invasively determined blood glucose level define the learning set λ of the device;

forming, from a plurality of learning vectors, an M by N regular learning matrix, λ, by using an output of repeated invasive measurements both of "(a)" and the non-invasive biometric reading of the tissue of "(b)" so as to acquire N vectors in the learning set, wherein N is determined according to the person's invasively determined blood glucose level;

implementing a noninvasive isolation mechanism of the tissue glucose level by unique association of the vector $V_k$ with an invasive blood glucose level, wherein the association is defined as $V_k \rightarrow g_k$, wherein if $V_k = V_n$ then $g_k = g_n$ for any k≠n, where $g_k$ and $g_n$ are the invasively determined blood glucose level references of the person and $V_k$ is a vector in the learning set λ, and discard vectors $V_k$ that fail the noninvasive isolation association;

determining a neural network from the learning set λ by pairing vectors into a branch and forming multiple branches into loops, wherein two vectors are paired if they have a pre-defined similarity in the blood glucose levels that each are associated with (for example the glucose levels of each of the two vectors are sufficiently close to one another); and calibrating the neural network by having the neural network pass at least one internal blind test.

In some embodiments, the program code also performs a first internal blind test, of the at least one internal blind test, comprising:

(a) temporarily excluding a pre-determined minority of vectors {V} from the learning set λ and the remaining majority of vectors {V} in the learning set λ is used to determine a current neural network while treating the excluded set of vectors {V} as a set of new vectors {$V^{new}$} and (b) determining for each excluded vector $V^{new}$ an optimal correlated loop of vectors in the current neural network wherein the invasive glucose levels previously associated with the optimal correlated loop is used to determine noninvasively the momentary glucose level $ng_k$ to be associated with each vector $V^{new}$ of the excluded minority as the noninvasive reading.

In some embodiments, the program code also performs a second internal blind test by (a) excluding a single vector V from the learning set λ, reconstituted after the first blind test, wherein the remaining supermajority of vectors {V} in the learning set λ is used to determine a second current neural network while treating the excluded vector V as a new vector $V^{new}$ and (b) determining a further optimal correlated loop of vectors in the second current neural network and using the invasive glucose levels previously associated with the further optimal loop to determine noninvasively the momentary glucose level $ng_k$.

In some embodiments, the program code also repeats the second internal blind test cyclically for all vectors in the learning set λ.

In some embodiments, the program code declares the device calibrated if the first and second internal blind tests pass an internal accuracy requirement defined by the differences between the noninvasive reading $ng_k$ and the invasive reading $g_k$ associated with each vector in the learning set λ.

In some embodiments, the program code also post-calibrates the device by obtaining, a new vector, $V^{new}$ by non-invasively measuring a body location of the person by using the one or more color image sensors in the non-invasive component to generate a series of images acquired from the one or more color image sensors of tissue of the body part, and converting the series of images into a new vector $V^{new}$, and finding an optimal correlated loop of the calibrated neural network with the new vector, $V^{new}$ and using the invasive glucose levels $g_k$ associated with the vectors in the optimal correlated loop of the calibrated neural network to compute noninvasively the glucose level $ng_{new}$ to be associated with the new vector $V^{new}$.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:
1. A method of monitoring a blood glucose of a person, comprising:

(a) (i) invasively measuring the blood glucose of the person using an invasive component of a bioparameter monitoring device, storing an invasive blood glucose measurement, $g_{k1}$, in a non-invasive component of the bioparameter monitoring device;

(b) within a proximity time before or after step "(a)", one or more color image sensors in the non-invasive component of the device generating a series of images reflecting absorption of light having traversed tissue of a body part of the person, the series of images converted into a vector V, wherein the vector V is associated with a particular at least one invasive blood glucose measurement $g_{k1}$, describing a momentary glucose level in the person's blood and a set of all the vectors, each vector in the set identified as V, associated with an invasively determined blood glucose level define a learning set λ of the device;

from a plurality of learning vectors, forming, by one or more processors, an M by N regular learning matrix, λ, by repeating steps "(a)" through "(b)" so as to acquire N vectors in the learning set, wherein N is determined according to the person's invasively determined blood glucose level;

(c) implementing a noninvasive isolation mechanism of a tissue glucose level by unique association of a vector $V_k$ with an invasive blood glucose level, wherein the association is defined as $V_k \rightarrow g_k$, wherein if $V_k = V_n$ then $g_k = g_n$ for any k≠n, where $g_k$ and $g_n$ are invasively determined blood glucose level references of the person and $V_k$ is a vector in the learning set λ, and discarding any vectors $V_k$ that fails the noninvasive isolation mechanism's association;

(d) determining, by the one or more processors, a neural network from the learning set λ by pairing vectors into a branch and forming multiple branches into loops, wherein two vectors are paired if they have a pre-defined similarity in the blood glucose levels that each are associated with; and (e) calibrating the neural network by having the neural network pass at least one internal blind test.

2. The method of claim 1, further comprising a first internal blind test, of the at least one internal blind test, that comprises:

(a) temporarily excluding a pre-determined minority of vectors V from the learning set λ and a remaining majority of vectors V in the learning set λ is used to determine a current neural network while treating an excluded set of vectors V as a set of new vectors $V^{new}$ and (b) determining for each excluded vector $V^{new}$ an optimal correlated loop of vectors in the current neural network wherein invasive glucose levels previously associated with an optimal correlated loop are used to determine noninvasively the momentary glucose level $ng_k$ to be associated with each vector $V^{new}$ of an excluded minority as a noninvasive reading.

3. The method of claim 1, further comprising performing a second internal blind test of the at least one internal blind test by (a) excluding a single one of the vectors V from the learning set λ, reconstituted after a first internal blind test of the at least one internal blind test, wherein a remaining supermajority of vectors V in the learning set λ is used to determine a second neural network, the second neural network being a current neural network, while treating the excluded vector V as a new vector $V^{new}$ and (b) determining an optimal correlated loop of vectors in the second current neural network and using invasive glucose levels previously associated with a further optimal loop to determine noninvasively the momentary glucose level $ng_k$.

4. The method of claim 3, wherein the second internal blind test is repeated cyclically for all vectors in the learning set λ.

5. The method of claim 1, wherein the device is declared calibrated whenever first and second internal blind tests of the at least one internal blind test pass an internal accuracy requirement defined by the differences between the momentary glucose level $ng_k$ determined noninvasively and the invasive blood glucose measurement $g_k$ associated with each vector in the learning set λ.

6. The method of claim 1, further comprising, post-calibrating the device by, the one more processors obtaining, a new vector, $V^{new}$ by non-invasively measuring a body location of the person by using the one or more color image sensors in the non-invasive component to generate a series of images acquired from the one or more color image sensors of tissue of the body part, and converting the series of images into the new vector $V^{new}$, and finding an optimal correlated loop of the calibrated neural network with the new vector, $V^{new}$ and using the invasive glucose levels $g_k$ associated with the vectors in the optimal correlated loop of the calibrated neural network to compute noninvasively the glucose level $ng_{new}$ to be associated with the new vector $V^{new}$.

7. The method of claim 1, further comprising (a) (ii) repeating step "(a)(i)" to produce at least an additional invasive blood glucose measurement, $g_{k2}$, and requiring $g_{k2}$ to be sufficiently close to $g_{k1}$ by a pre-defined measure of closeness.

8. An apparatus for monitoring a blood glucose of a person, comprising:

(a) an invasive component configured for (i) invasively measuring the blood glucose of the person using an invasive component of a bioparameter monitoring device, storing an invasive blood glucose measurement, $g_{k1}$, in a non-invasive component of the bioparameter monitoring device;

(b) a non-invasive component structured to receive a body part of the person and configured to generate a non-invasive blood glucose reading of tissue of the body part upon insertion of the body part of the patient into the non-invasive component, the non-invasive component including one or more color image sensors configured to generate a series of images reflecting absorption of light that traversed the tissue, the device having one or more processors programmed using program code to:

convert the series of images into a vector V, wherein the vector V is associated with a particular at least one invasive blood glucose measurement $g_{k1}$, describing a momentary glucose level in the person's blood and a set of all the vectors, each vector in the set identified as V, associated with an invasively determined blood glucose level define a learning set λ of the device;

form, from a plurality of learning vectors, an M by N regular learning matrix, λ, by using an output of repeated invasive measurements both of "(a)" and the non-invasive blood glucose reading of the tissue of "(b)" so as to acquire N vectors in the learning set, wherein N is determined according to the person's invasively determined blood glucose level;

implement a noninvasive isolation mechanism of a tissue glucose level by unique association of the vector $V_k$ with an invasive blood glucose level, wherein the association is defined as $V_k \rightarrow g_k$, wherein if $V_k = V_n$ then $g_k = g_n$ for any $k \neq n$, where $g_k$ and $g_n$ are invasively determined blood glucose level references of the person and $V_k$ is a vector in the learning set $\lambda$, and discard any vector $V_k$ that fails the noninvasive isolation mechanism's association;

determine a neural network from the learning set $\lambda$ by pairing vectors into a branch and forming multiple branches into loops, wherein two vectors are paired if they have a pre-defined similarity in the blood glucose levels that each are associated with; and calibrate the neural network by having the neural network pass at least one internal blind test.

9. The apparatus of claim 8, wherein the one or more processors are also programmed using program code to conduct a first internal blind test, of the at least one internal blind test, comprising:

(a) temporarily excluding a pre-determined minority of vectors V from the learning set X and a remaining majority of vectors V in the learning set X is used to determine a current neural network while treating an excluded set of vectors V as a set of new vectors $V^{new}$ and (b) determining for each excluded vector $V^{new}$ an optimal correlated loop of vectors in the current neural network wherein invasive glucose levels previously associated with the optimal correlated loop are used to determine noninvasively the momentary glucose level $ng_k$ to be associated with each vector $V^{new}$ of an excluded minority as a noninvasive reading.

10. The apparatus of claim 8, wherein the one or more processors are also programmed using program code to conduct a second internal blind test of the at least one internal blind test by (a) excluding a single one of the vectors V from the learning set $\lambda$, reconstituted after the first blind test, wherein a remaining supermajority of vectors V in the learning set $\lambda$ is used to determine a second neural network, the second neural network being a current neural network, while treating the excluded vector V as a new vector $V^{new}$ and (b) determining an optimal correlated loop of vectors in the second current neural network and using invasive glucose levels previously associated with a further optimal loop to determine noninvasively the momentary glucose level $ng_k$.

11. The apparatus of claim 10, wherein the second internal blind test is repeated cyclically for all vectors in the learning set $\lambda$.

12. The apparatus of claim 8, wherein the device is declared calibrated if first and second internal blind tests of the at least one internal blind test pass an internal accuracy requirement defined by the differences between the noninvasive reading $ng_k$ and the invasive reading $g_k$ associated with each vector in the learning set $\lambda$.

13. The apparatus of claim 8, wherein the one or more processors are also programmed using program code to post-calibrate the device by obtaining, a new vector, $V^{new}$ by non-invasively measuring a body location of the person by using the one or more color image sensors in the non-invasive component to generate a series of images acquired from the one or more color image sensors of tissue of the body part, and converting the series of images into the new vector $V^{new}$, and finding an optimal correlated loop of a calibrated neural network with the new vector, $V^{new}$ and using the invasive glucose levels $g_k$ associated with the vectors in the optimal correlated loop of the calibrated neural network to compute noninvasively the glucose level $ng_{new}$ to be associated with the new vector $V^{new}$.

14. The apparatus of claim 8, wherein the invasive component is configured for (ii) repeating the invasive measurement of "(i)" to produce at least an additional invasive blood glucose measurement, $g_{k2}$, and requiring $g_{k2}$ to be sufficiently close to $g_{k1}$ by a pre-defined measure of closeness.

15. A non-transitory computer-readable medium having stored thereon glucose monitoring software, the glucose monitoring software executed by one or more processors, the execution of the glucose monitoring software by the one or more processors performing:

(a) storing an invasive blood glucose measurement, $g_{k1}$, in a non-invasive component of a glucose monitoring device;

(b) receiving a series of images from one or more color image sensors reflecting absorption of light that traversed tissue of a body part of a person, converting the series of images into a vector V, wherein the vector V is associated with a particular at least one invasive blood glucose measurement $g_{k1}$, describing a momentary glucose level in the person's blood and a set of all the vectors, each vector in the set identified as V, associated with an invasively determined blood glucose level define a learning set $\lambda$ of the device;

(c) forming, from a plurality of learning vectors, an M by N regular learning matrix, $\lambda$, by using an output of repeated invasive blood glucose measurements both of "(a)" and the non-invasive blood glucose measurement of the tissue of "(b)" so as to acquire N vectors in the learning set, wherein N is determined according to the person's invasively determined blood glucose level;

(d) implementing a noninvasive isolation mechanism of a tissue glucose level by unique association of the vector $V_k$ with an invasive blood glucose level, wherein the association is defined as $V_k \rightarrow g_k$, wherein if $V_k = V_n$ then $g_k = g_n$ for any $k \neq n$, where $g_k$ and $g_n$ are invasively determined blood glucose level references of the person and $V_k$ is a vector in the learning set $\lambda$, and discard any vectors $V_k$ that fails the noninvasive isolation mechanism's association;

(e) determining a neural network from the learning set $\lambda$ by pairing vectors into a branch and forming multiple branches into loops, wherein two vectors are paired if they have a pre-defined similarity in the blood glucose levels that each are associated with; and (f) calibrating the neural network by having the neural network pass at least one internal blind test.

16. The medium of claim 15, wherein the execution of the glucose monitoring software also performs:

a first internal blind test, of the at least one internal blind test, comprising:

(a) temporarily excluding a pre-determined minority of vectors V from the learning set $\lambda$ and a remaining majority of vectors V in the learning set $\lambda$ is used to determine a current neural network while treating an excluded set of vectors V as a set of new vectors $V^{new}$ and (b) determining for each excluded vector $V^{new}$ an optimal correlated loop of vectors in the current neural network, wherein the invasive glucose levels previously associated with the optimal correlated loop is used to determine noninvasively the momentary glucose level $ng_k$ to be associated with each vector $V^{new}$ of the excluded minority as a noninvasive reading.

17. The medium of claim 15, wherein the execution of the glucose monitoring software also performs a second internal blind test of the at least one internal blind test by
  (a) excluding a single one of the set of all the vectors, each vector in the set identified as V, from the learning set λ, reconstituted after the first blind test of the at least one internal blind test, wherein a remaining supermajority of vectors V in the learning set λ is used to determine a second neural network, the second neural network being a current neural network, while treating an excluded vector V as a new vector $V^{new}$ and
  (b) determining an optimal correlated loop of vectors in the second current neural network and using the invasive glucose levels previously associated with a further optimal loop to determine noninvasively the momentary glucose level $ng_k$.

18. The medium of claim 17, wherein the execution of the glucose monitoring software also repeats the second internal blind test cyclically for all vectors in the learning set λ.

19. The medium of claim 15, wherein the execution of the glucose monitoring software declares the device calibrated if a first internal blind test and a second internal blind test of the at least one internal blind test pass an internal accuracy requirement defined by the differences between the noninvasive reading $ng_k$ and the invasive reading $g_k$ associated with each vector in the learning set λ.

20. The medium of claim 15, wherein the program code also post-calibrates the device by obtaining, a new vector, $V^{new}$ by non-invasively measuring a body location of the person by using the one or more color image sensors in the non-invasive component to generate a series of images acquired from the one or more color image sensors of tissue of the body part, and converting the series of images into the new vector $V^{new}$, and finding an optimal correlated loop of a calibrated neural network with the new vector, $V^{new}$ and using the invasive glucose levels $g_k$ associated with the vectors in the optimal correlated loop of the calibrated neural network to compute noninvasively the glucose level $ng_{new}$ to be associated with the new vector $V^{new}$.

21. The medium of claim 15, wherein the execution of the glucose monitoring software by the one or more processors also performs: storing an additional invasive blood glucose reading, $g_{k2}$, and requiring $g_{k2}$ to be sufficiently close to $g_{k1}$ by a pre-defined measure of closeness.

* * * * *